United States Patent
Kolari et al.

(10) Patent No.: US 9,272,927 B2
(45) Date of Patent: Mar. 1, 2016

(54) METHOD FOR PREVENTING GROWTH OF MICROORGANISMS, AND A COMBINATION FOR THE PREVENTION OF MICROBIAL GROWTH

(75) Inventors: Marko Kolari, Vantaa (FI); Antti Heinänen, Imatra (FI)

(73) Assignee: KEMIRA, OYJ, Helsinki (FI)

( * ) Notice: Subject to any disclaimer, the term of this patent is extended or adjusted under 35 U.S.C. 154(b) by 1413 days.

(21) Appl. No.: 12/447,349

(22) PCT Filed: Nov. 7, 2007

(86) PCT No.: PCT/FI2007/000270
§ 371 (c)(1),
(2), (4) Date: Jun. 28, 2010

(87) PCT Pub. No.: WO2008/056025
PCT Pub. Date: May 15, 2008

(65) Prior Publication Data
US 2010/0267791 A1    Oct. 21, 2010

(30) Foreign Application Priority Data

Nov. 9, 2006    (FI) .................................. 20060986

(51) Int. Cl.
| | |
|---|---|
| A01N 43/50 | (2006.01) |
| C02F 1/50 | (2006.01) |
| A01N 37/16 | (2006.01) |
| A01N 59/00 | (2006.01) |
| C02F 1/66 | (2006.01) |
| C02F 1/76 | (2006.01) |

(52) U.S. Cl.
CPC . *C02F 1/50* (2013.01); *A01N 37/16* (2013.01); *A01N 43/50* (2013.01); *A01N 59/00* (2013.01); *C02F 1/66* (2013.01); *C02F 1/766* (2013.01)

(58) Field of Classification Search
USPC ...................................................... 514/389
See application file for complete search history.

(56) References Cited

U.S. PATENT DOCUMENTS

| | | | |
|---|---|---|---|
| 3,329,610 A | * | 7/1967 | Kreuz et al. ................. 166/275 |
| 5,736,057 A | * | 4/1998 | Minotti ........................ 210/759 |
| 5,980,758 A | | 11/1999 | LaZonby et al. |
| 6,211,237 B1 | * | 4/2001 | Huss et al. .................... 514/557 |
| 6,866,749 B2 | * | 3/2005 | Delmas et al. .................. 162/56 |
| 2006/0049119 A1 | * | 3/2006 | Ludensky et al. ............. 210/755 |

FOREIGN PATENT DOCUMENTS

| | | |
|---|---|---|
| WO | 03062149 | 7/2003 |
| WO | 2004026770 | 4/2004 |
| WO | 2006097578 | 9/2006 |
| WO | 2007011445 | 1/2007 |
| WO | WO 2007011445 A2 * | 1/2007 |

OTHER PUBLICATIONS https://noppa.lut.fi/noppa/opintojakso/.../biocides_case_study.pdf downloaded Aug. 28, 2014.*
International Search Report; International Application No. PCT/FI2007/000270; International Filing Date Nov. 7, 2007; 3 pages.
Written Opinion of the International Searching Authority; International Application No. PCT/FI2007/000270; International Filing Date Nov. 7, 2007; 6 pages.
JP07299468; Nov. 14, 1995; Abstract Only (1 page).
Rogatina, L. N. et al: "Study of various chemical compounds for disinfection and preservation of small-scale water-purification plants", XP002497244, 1983, Abstract Only (1 page).
Naidenova, L. P. et al: "Study of new preparations for the sanitation treatment of technological equipment", XP002497245, 1979, Abstract Only (1 page).
Zhang, Yingchun et al: "Examination of synergistic germicidal efficacy of peracetic acid and dichloromethyl hydantion", XP002497246, 2005, Abstract Only (1 page).
Shen, Jianzhong et al: Experimental observation on bactericidal efficacy and corrosiveness of compound disinfectant of peracetic acid, XP002497247, 2004, Abstract Only (1 page).

* cited by examiner

*Primary Examiner* — Shirley V Gembeh
(74) *Attorney, Agent, or Firm* — Thomas Horstemeyer, LLP

(57) ABSTRACT

According to the invention, a method for the prevention of microbial growth in process waters is provided, wherein first a peracid compound, and thereafter a halogenated dialkyl hydantoin are dosed into said process water. Further, according to the invention, a combination for the prevention of microbial growth is provided, said combination comprising compounds to be dosed separately, said compounds being a peracid compound to be dosed first, and a halogenated dialkyl hydantoin to be dosed after the peracid compound, the weight ratio of the peracid compound to the halogenated dialkyl hydantoin being at least 2:1, wherein the amount of the peracid compound is calculated as active agent, while the amount of halogenated dialkyl hydantoin is calculated as active chlorine.

12 Claims, 3 Drawing Sheets

Figure 1:
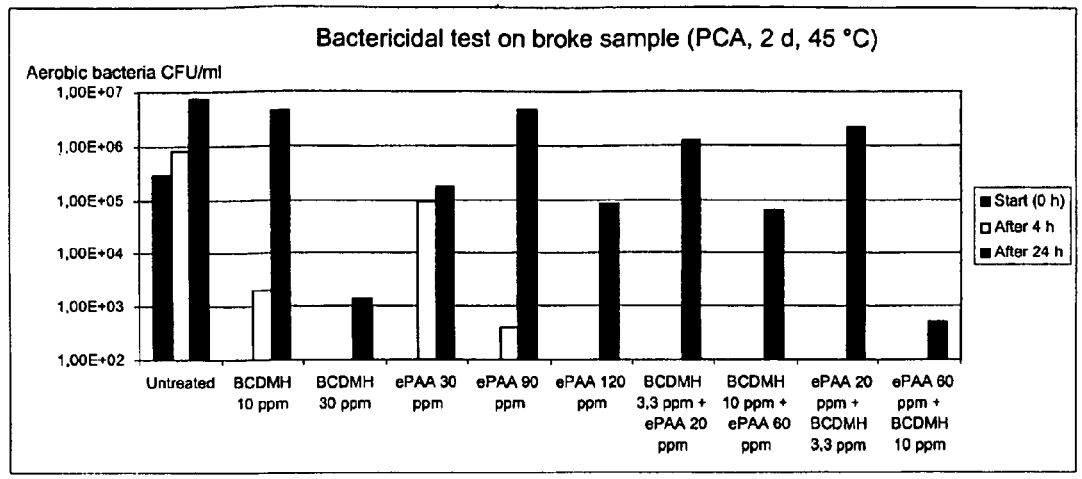

METHOD FOR PREVENTING GROWTH OF MICROORGANISMS, AND A COMBINATION FOR THE PREVENTION OF MICROBIAL GROWTH

CROSS REFERENCE TO RELATED APPLICATIONS

This is a U.S. national stage of application No. PCT/FI2007/000270, filed on 7 Nov. 2007. Priority under 35 U.S.C. §119(a) and 35 U.S.C. §365(b) is claimed from Finland Patent Application No. 20060986, filed 9 Nov. 2006, the disclosure of which is also incorporated herein by reference.

The invention relates to a method for preventing microbial growth in process waters. Moreover, the invention is directed to a combination for the prevention of microbial growth. The invention is particularly suitable for the treatment of industrial process waters, including the treatment of raw and cooling waters. Preferred applications comprise processes of pulp and paper industries, including water circuits of paper and board machines, chemical pulp production plants, and deinking plants, and further, cooling water systems.

PRIOR ART

Peracetic acid is a commonly known biocide. Compared to other biocides, peracetic acid is very inexpensive. In practice it was, however, found that if peracetic acid is the only biocide used, the efficiency thereof is reduced in the long run due to selection of microbes on the paper machine producing higher amounts of extracellular material preventing the penetration of peracetic acid, thus lowering the killing activity thereof.

The document WO 2006/097578 A1 (BIM KEMI AB) discloses a combination of an oxidizing agent comprising chlorine with a bromine source for the prevention of microbial growth in raw or circulated waters of paper production processes. A preferable oxidizing agent is sodium hypochlorite, whereas a preferable bromine source is bromochlorodimethyl hydantoin (BCDMH) or dibromodimethyl hydantoin (DBDMH). The optimal amount of the oxidizing agent and bromine source, based on halogen, corresponds to the molar ratio of about 1:1. Use of said combination is associated with risks, that is, corrosion of the equipment is accelerated, and high amounts of hypochlorite used are likely to increase the formation of AOX compounds detrimental to the environment. In addition, hypochlorite used in great amounts has adverse effects on the papermaking chemistry.

A mixture of peracetic acid and dichlorodimethyl hydantoin is known from the document Chinese Journal of Disinfection 2003: 20(4), pages 276-278, where said mixture is said to have synergistic spore destroying activity. In this document, a solution containing 500 mg/l of peracetic acid and 300 mg/l of dichlorodimethyl hydantoin (as active chlorine) was studied. Among other things, the test results showed that the mixture was able to kill 100% of the spores of the bacteria *Bacillus subtilis* var. *niger*. It was also active against the bacteria *Escherichia coli* and *Staphylococcus aureus*. Weight ratio of peracetic acid to dichlorodimethyl hydantoin (as active chlorine) was about 1.67:1. A mixture containing considerable amounts of dichlorodimethyl hydantoin is not cost effective. Further, such a concentrated solution may cause corrosion, and for this reason, a corrosion inhibitor was added to said solution. The document suggests the use of said solution as a disinfectant.

A composition for the prevention of microbial growth in industrial process waters is known from U.S. Pat. No. 5,980,758 (Nalco Chemical Company), said composition containing peracetic acid and a non-oxidizing biocide. Peracetic acid is said to improve the activity of the non-oxidizing biocide. Said non-oxidizing biocide is benzisothiazoline, carbonimidic dibromide, 1,4-bis(bromoacetoxy)-2-butene or β-bromo-β-nitrostyrene. Peracetic acid may be added to process waters prior to the addition of the non-oxidizing biocide.

A composition for the prevention of microbial growth in industrial process waters is known from the document WO 03/062149 (Lonza Inc.), said composition containing an oxidizing or a non-oxidizing biocide, and a triamine compound. Suitable oxidizing biocides include, for example, peracetic acid, ozone, hypochlorite, chlorine dioxide, bromochlorodimethyl hydantoin, dichloromethylethyl hydantoin, dichlorodimethyl hydantoin, etc.

Peracetic acid is widely used for the prevention of microbes on paper machines. As a problem, it has now however been found that peracetic acid alone is not enough to provide a long-lasting biocidal activity, that is, it needs another biocide as a booster. Compounds known from the above documents are, however, associated with drawbacks that will be eliminated by the present invention.

An object of the invention is to provide a cost effective method for the prevention of microbes that is acceptable for the environment and non-corrosive in comparison e.g. to hypochlorite or concentrated solutions.

DESCRIPTION OF THE INVENTION

It has now been found that an excellent net effect is achieved by first dosing inexpensive peracetic acid or another peracid to process waters for killing most of the microbes present by an agent that is environmentally acceptable and non-corrosive in comparison to e.g. hypochlorite, followed by the dosage of a minor amount of halogenated dialkyl hydantoin penetrating more efficiently into microbial cells than peracetic acid, thus making sure that also slightly more resistant microbes get killed.

Thus, according to the invention, a method for the prevention of microbial growth in process waters is provided, wherein first a peracid compound and thereafter a halogenated dialkyl hydantoin are dosed into said process water.

Said peracid compound may be an organic peracid compound or percarbonate.

Said organic peracid compound is preferably peracetic acid or performic acid, or a mixture thereof. Peracetic acid may be an equilibrium solution thereof, or distilled peracetic acid.

Sodium percarbonate is a preferable percarbonate.

Alkyl groups in halogenated dialkyl hydantoin may be identical or different, being preferably methyl or ethyl. Halogen substituent at position 1 or 3 is preferably chloro or bromo. Preferable halogenated dialkylhydantoins include monochlorodimethyl hydantoin (MCDMH), dichlorodimethyl hydantoin (DCDMH), bromochlorodimethyl hydantoin (BCDMH), dibromodimethyl hydantoin (DBDMH) or dichloromethylethyl hydantoin (DCMEH), or a mixture thereof.

Weight ratio of the peracid compound to halogenated dialkyl hydantoin is preferably at least 2:1, the amount of the peracid compound being calculated as active agent, while the amount of halogenated dialkyl hydantoin is calculated as active chlorine.

Said ratio is preferably between 2:1 and 125:1, more preferably between 2:1 and 75:1, and most preferably between 2.5:1 and 30:1.

Peracid compound may be dosed in an amount of 0.2 to 45 mg/l, preferably 0.2 to 30 mg/l and more preferably 0.2 to 15 mg/l, calculated as active agent.

Halogenated dialkyl hydantoin may be dosed in an amount of 0.1 to 25 mg/l, preferably 0.2 to 15 mg/l, and more preferably 0.2 to 6 mg/l, calculated as active chlorine.

The total amount of the peracid compound and halogenated dialkyl hydantoin may range between 0.3 and 70 mg/l, preferably between 0.4 and 45 mg/l.

According to the invention, also a combination for the prevention of microbial growth is provided, said combination comprising compounds to be dosed separately, said compounds being a peracid compound to be dosed first, and a halogenated dialkyl hydantoin to be dosed after the peracid compound, the weight ratio of the peracid compound to the halogenated dialkyl hydantoin being at least 2:1, wherein the amount of the peracid compound is calculated as active agent, while the amount of halogenated dialkyl hydantoin is calculated as active chlorine.

Preferred components of the inventive combination and preferred amounts are defined above.

According to the invention, the peracid compound is dosed first, followed by the treatment of the process water treated with said peracid compound with the halogenated dialkyl hydantoin prior to attenuation of the activity of the peracid, without an extended interval between the treatments. In case of flowing process waters this is preferably carried out by dosing the peracid compound for instance at suction side of a pump resulting in rapid and efficient mixing, followed by the dosage of said halogenated dialkyl hydantoin in the same pipeline after the pump, or to the next tank. The solution of choice depends among other things on the flow rate, and it is crucial the treatment is directed to the substantially same water fraction. The interval between the dosages of the peracid compound and halogenated dialkyl hydantoin may be from 0.5 seconds to 60 minutes, preferably from 10 seconds to 60 minutes, more preferably between 20 seconds and 30 minutes.

According to the invention, it is also possible to dose said peracid compound and halogenated dialkyl hydantoin at the same point such as tank, said peracid compound being dosed first, followed by said halogenated dialkyl hydantoin after the interval defined above.

The dosage of said peracid compound may be continuous or intermittent. The dosage of said halogenated dialkyl hydantoin may be continuous or intermittent. In case of intermittent dosage, it is substantial for the desired effect according to the invention that said halogenated dialkyl hydantoin is dosed into to the same water fraction as said peracid compound dosed first.

According to the invention, by first dosing the less expensive peracetic acid, redox of process waters can be increased, and thus most of the microbes can be killed by an environmentally acceptable agent less corrosive than hypochlorite. Thus, the more expensive halogenated dialkyl hydantoin to be dosed after a predetermined interval is not consumed in undue reactions with reducing compounds irrelevant to microbes. Efficient killing and prevention of rapid regrowth of microbes can be guaranteed with only low amounts of halogenated dialkyl hydantoin since these compounds are able to penetrate into microbial cells efficiently, thus making sure that also more resistant microbes get killed.

For the prevention of biofilms according to the invention, the combination of peracetic acid and MCDMH is particularly preferred. For killing freely swimming microbes, the combination of peracetic acid and BCDMH is particularly preferred.

The invention is directed to the prevention of microbial growth, all microorganisms present in process waters generally being targeted, such as aerobic bacteria, facultatively anaerobic bacteria, sulfate reducing bacteria, filamentous bacteria, bacteria forming biofilms, yeasts, molds, and protozoa.

The invention is particularly suitable for the treatment of process waters including raw waters and water in cooling systems. Particularly suitable applications include circulated waters in the production of paper and board, chemical, or reclaimed paper pulps, circulated cooling waters, and waters in cooling towers. Other applications include cooling and circulating waters in food industry and metal industry, and further waters in cooling systems of hospitals (prevention of the bacterium *Legionella*). The invention is also useful for the treatment of ballast waters of ships. Yet another application comprises waters in oil fields.

The invention is now described with reference to the appended drawings where

Figure 2:
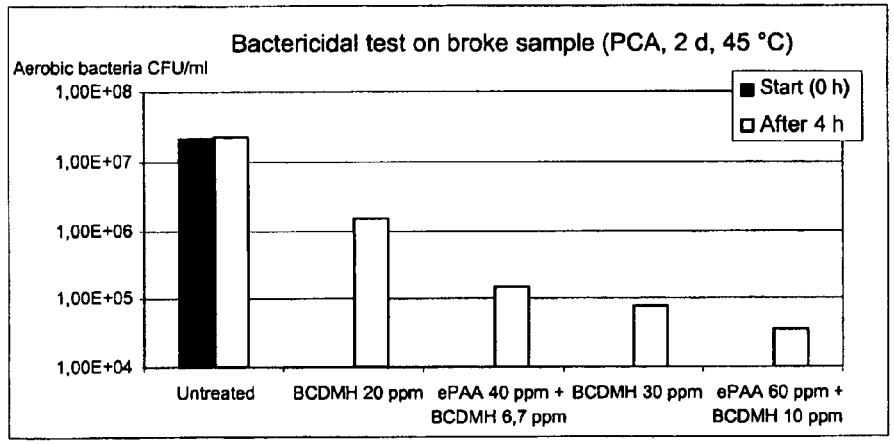
Figure 3:
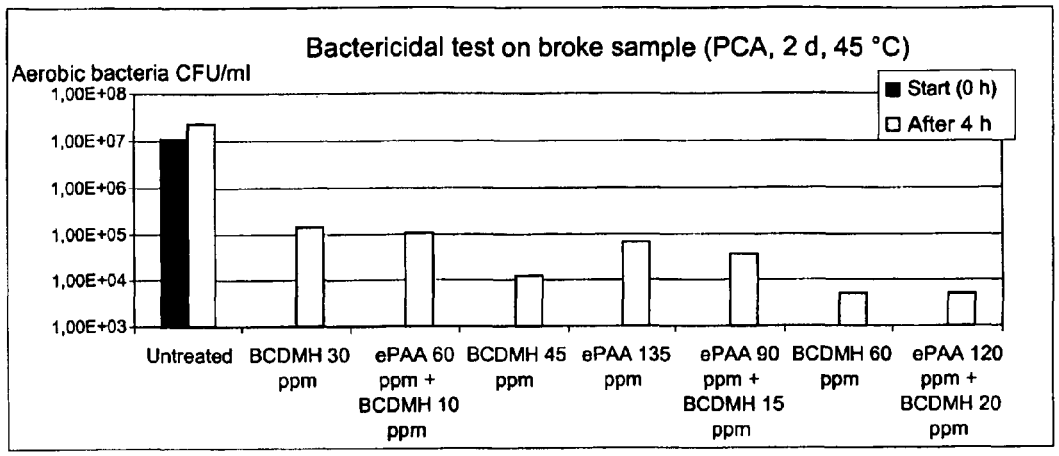
Figure 4:
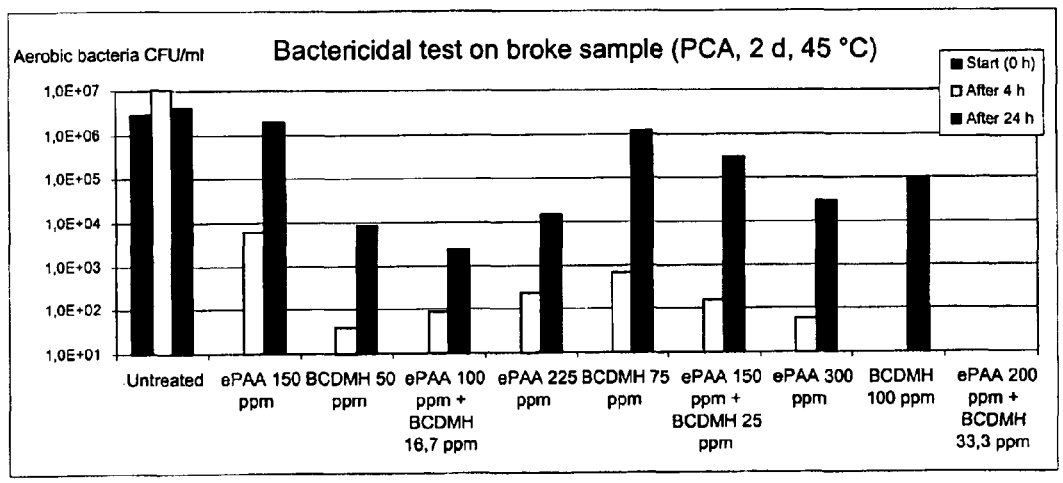

FIG. 1 shows testing of bactericidal activity against aerobic bacteria present in broke where killing efficacy of BCDMH and ePAA used alone and in combination were compared, FIG. 2 shows testing of bactericidal activity against aerobic bacteria present in broke where efficacy of BCDMH, and combinations of ePAA+BCDMH were compared, FIG. 3 shows testing of bactericidal activity against aerobic bacteria present in broke where killing efficacy of BCDMH and ePAA used alone and in combination were compared, and FIG. 4 shows testing of bactericidal activity against aerobic bacteria present in wire pulper sample where killing efficacy of BCDMH and ePAA used alone and in combination were compared.

Figure 5:
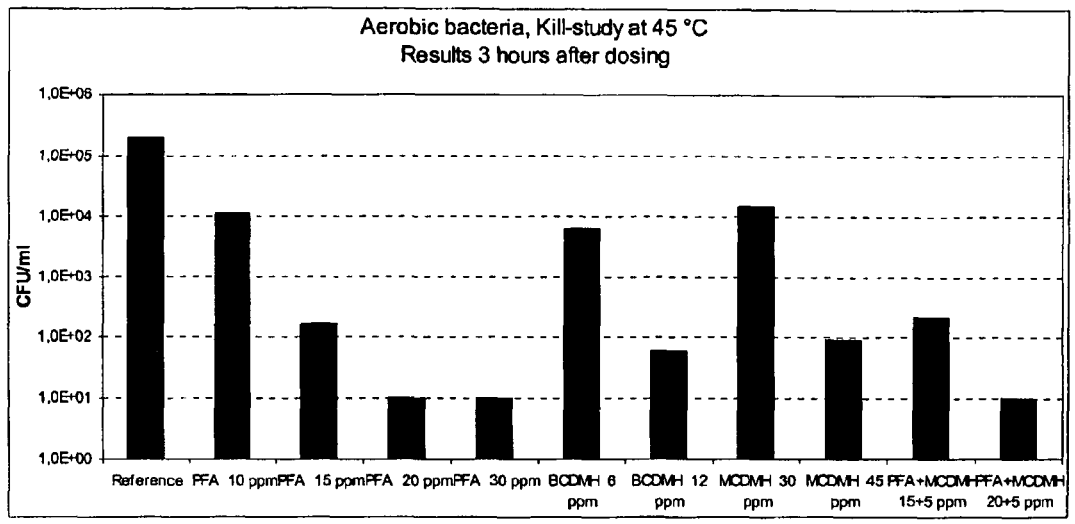
Figure 6:
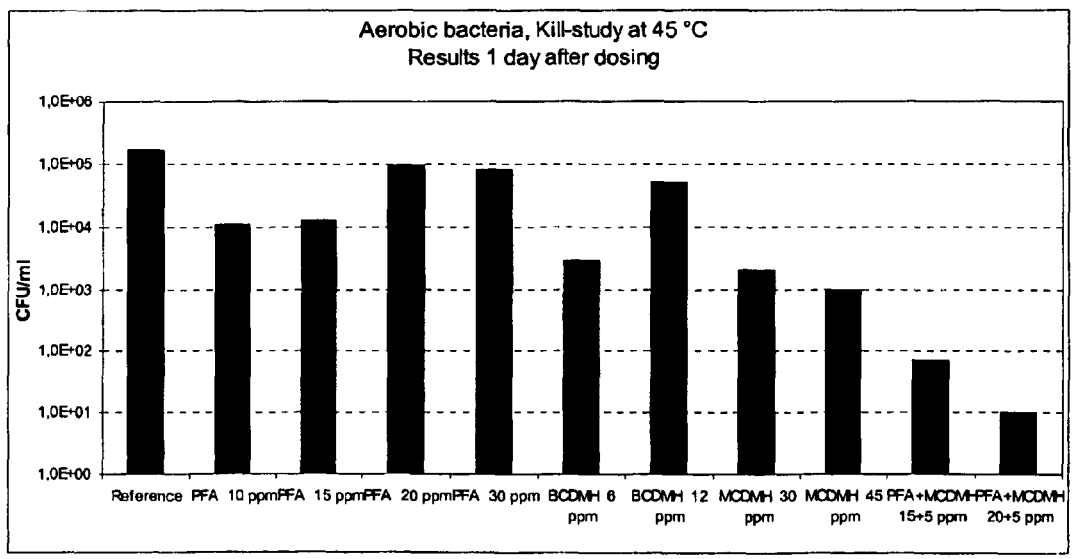

FIGS. 5 and 6 show testing of bactericidal activity against aerobic bacteria present in circulation water from an alkaline fine paper machine where killing efficacy of BCDMH, MCDMH and PFA used alone and in combination were compared.

In some of the tests shown below, the combination of ePAA+BCDMH provides evident synergy in biocidal activity, that is, the result is better when the compounds are used together. In some of the tests, the activity seems to be similar, but a cost reduction of several tens of percents is obtained when expenses are taken into consideration.

ePAA, BCDMH and MCDMH used in tests are commercially available products.

Equilibrium solution of peracetic acid used, ePAA, had the following composition: about 15% of peracetic acid, about 24% of acetic acid, and about 15% of hydrogen peroxide, all percentages being by weight.

The invention will now be described in more detail by means of examples. Note that in the examples, concentrations are expressed as concentrations of the products, and thus for instance 60 ppm of ePAA corresponds to about 9 ppm of PAA as active agent, 10 ppm of BCDMH corresponds to about 3 ppm of active chlorine, while 60 ppm of MCDMH corresponds to about 6 ppm of active chlorine.

EXAMPLE 1

Dilute broke of a board machine (pH 7.8, oxidation reduction potential (ORP) 40 mV) was divided into 10 separate jars, and biocides to be tested were dosed. Concentrations are expressed in ppm (mg/l) of the commercially available product. In tests where two different agents were dosed into a single jar, the jar was closed after the first pipetting, the broke sample was vigorously agitated, followed by the addition of the second agent during 5 to 10 minutes. Jars were incubated under conditions corresponding to those in the broke system (45° C., mixing), and thereafter, viable aerobic bacterial counts were determined by cultivation after exposure periods of 4 and 24 hours.

In this bactericidal test on broke, killing efficacy of BCDMH and ePAA used alone and in combinations were compared, two thirds of BCDMH being replaced in the combinations with peracetic acid used in threefold amounts. For instance BCDMH 10 ppm versus ePAA 30 ppm versus BCDMH 3.3 ppm+ePAA 20 ppm.

The results are summarized in FIG. 1. The combination "BCDMH 3.3 ppm+ePAA 20 ppm" means that BCDMH was added prior to ePAA.

In an untreated broke sample (control), aerobic bacterial count was increased during testing: initial bacterial count was $4 \times 10^6$ cfu/ml, compared to $7 \times 10^6$ cfu/ml 24 hours later.

Viable bacterial counts were clearly reduced by all added biocides after 4 hours of exposure. Comparison of killing efficacy after a contact time of 4 hours showed that combinations with 3.3 ppm of BCDMH and 20 ppm of ePAA were more efficient than BCDMH 10 ppm alone, or ePAA 30 ppm alone.

Most significant differences in results may be seen after a contact time of 24 hours. In most of the samples, strong regrowth was observed after exhaustion of the oxidizing biocide. Regrowth was inhibited more effectively by BCDMH 30 ppm than PAA alone. However, the best result was obtained with a combination comprising 60 ppm of peracetic acid dosed first, and 10 ppm of BCDMH dosed immediately after PAA. This order of dosage was considerably more efficient than the dosage of same amounts of chemicals in reversed order.

Based on the results, best long-lasting killing efficacy is achieved by dosing first PAA and immediately thereafter BCDMH. A better result is obtained by the use of this combination than by the dosage of only peracetic acid. Also BCDMH dosed alone is active, but however, the use of said combination yields the best cost efficiency since peracetic acid is a considerably less expensive chemical than BCDMH.

EXAMPLE 2

A sample (pH 7.9, ORP 145 mV) from a broke pulper of another board machine was divided in jars, followed by similar testing as described above.

In this bactericidal test on broke, killing efficacy of BCDMH, and combinations of ePPA+BCDMH were compared, two thirds of BCDMH being replaced in the combinations with peracetic acid used in threefold amounts.

The results are presented in FIG. 2.

Comparison of killing efficacy after 4 hours of exposure showed that a combination with 40 ppm of ePAA and 6.7 ppm of BCDMH was clearly more efficient than 20 ppm of BCDMH alone. Similarly, a combination with 60 ppm of ePAA and 6.7 ppm of BCDMH was more efficient than 30 ppm of BCDMH alone. The results suggest that improved results both with respect to killing efficacy and cost efficiency are obtained by using said combinations.

EXAMPLE 3

Dilute broke of a board machine (pH 7.5, ORP 130 mV) was divided into jars, followed by similar testing as described above.

In this bactericidal test on broke, killing efficacy of BCDMH and ePPA used either alone or in combinations were compared, two thirds of BCDMH being replaced in the combinations with peracetic acid used in threefold amounts.

The results are presented in FIG. 3.

Comparison of killing efficacy after a contact time of 4 hours showed that combinations of ePAA+BCDMH gave identical killing efficacy as BCDMH alone.

The results suggest that the use of said combination yields the best cost efficiency since peracetic acid is a considerably less expensive chemical than BCDMH.

EXAMPLE 4

A wire pulper sample (pH 7.9, ORP 46 mV) was divided into jars, followed by similar testing as above.

In this bactericidal test, killing efficacy of ePAA and BCDMH used either alone or in combinations were compared, two thirds of BCDMH being replaced in the combinations with peracetic acid used in threefold amounts.

The results are shown in FIG. 4.

In the tests, initial aerobic bacterial counts were about $3 \times 10^6$ cfu/ml. In all jars with added biocides, viable bacterial counts were clearly lower after four hours of exposure. Strong regrowth was observed in several jars after exhaustion of the oxidizing biocide (24 hours).

The best result was obtained with a combination comprising 200 ppm of peracetic acid dosed first, and 33.3 ppm of BCDMH dosed immediately after PAA. This combination was considerably more efficient than 100 ppm of BCDMH or 300 ppm of ePAA used alone. In cases lower amounts were used, combinations of ePAA+BCDMH in amounts of 100 ppm+16.7, and 150 ppm+25 ppm were identical in activities with 50 ppm, or 75 ppm of BCDMH alone, respectively.

The results suggest that the use of combinations of peracetic acid and BCDMH yields the best results both with respect to killing efficacy, and cost efficiency.

EXAMPLE 5

A test for destructing a biofilm was performed as described in the document FI 117056 B (Kemira Oyj). A biofilm was pregrown on lidplates having stainless steel pegs (3 d, 45° C., agitation at 150 rpm.). Clear filtrate of a fine paper machine served as the water (pH 7.6, ORP 71 mV), while a mixture of adherent bacteria (*Deinococcus geothermalis*, *Pseudoxanthomonas taiwanensis* and *Meiothermus silvanus*) grown in the laboratory was used for inoculation. After identical biofilms were grown on all the pegs of the lids, the lids were removed from the clear filtrate used for cultivation, washed with tap water and placed on plastic plates with 12 wells, one peg per well. 3.5 ml of the clear filtrate from the same paper machine, and the biocides to be tested were added in advance to each well. The pegs with biofilms were first immersed into the wells for 15 minutes, followed by removal of the plates for a moment for the addition of the other components of the biocidal combinations to the wells. Exposure to biocides was continued to attain a total contact time of 3 hours. Then, viability of the biofilms was determined by transferring the peglids to fresh 12-well plates where each well contained 2 ml of sterile cultivation broth, followed by cultivating the plates for 19 hours at 45° C. while mixing at 150 rpm. During this stage, survived biofilm bacteria formed a new biofilm on the walls of the wells of the clean plate. It was thus possible to evaluate the efficiency of the biocide treatments for biofilm destruction by comparing the extent of the new biofilms formed on the walls of the wells. To facilitate this evaluation, the wells were emptied, followed by staining of the biofilms with safranin.

The test results show that great amounts of biofilm were formed in the untreated control wells (++++).

Formation of new biofilm was not reduced by 120 ppm of the ePAA product (equilibrium solution of peracetic acid), or 60 ppm of MCDMH (monochlorodimethyl hydantoin) when used alone (++++). When used alone, 16 ppm of BCDMH (bromochlorodimethyl hydantoin) provided clearly reduced formation of the new biofilm, but not the complete inhibition thereof (++).

The only addition completely inhibiting the new biofilm (−) was a combination comprising 80 ppm of the equilibrium solution of peracetic acid, ePAA, dosed first, and 20 ppm of MCDMH dosed after ePAA.

It was shown in examples 1 to 4 that an improved killing efficacy against freely swimming microbes was achieved with the combination of ePAA+BCDMH. This result suggests that also an improved inhibiting activity against biofilms is provided by the combined use of peracetic acid and a halogenated dimethyl hydantoin (here MCDMH).

EXAMPLE 6

Circulation water (pH 8.2, ORP+169 mV) was collected from an alkaline fine paper machine (producing uncoated copy paper) and divided in 11 plastic containers. When two different biocides were dosed in to same container, the peracid was dosed first, the sample mixed thoroughly, and the second biocide was added within 5 to 10 minutes. All biocide dosages are reported as ppm (mg/l) of the commercial product, for example 20 ppm of performic acid (PFA) equilibrium product equals about 2 ppm as performic acid active substance, 12 ppm of BCDMH product equals about 4 ppm as active chlorine and 30 ppm of MCDMH product equals about 3 ppm as active chlorine. After biocide dosing the containers were capped and incubated at paper machine temperature (45° C.) with continuous agitation. The killing efficacy of different biocide dosages was measured 3 hours and 1 day after the biocide dosing using agar plate count method (PCA agar, 45° C., and 2 days).

Results are shown in FIGS. 5 and 6. Untreated reference sample contained cultivable aerobic bacteria $2.0 \times 10^5$ CFU/ml (3 h) and $1.6 \times 10^5$ CFU/ml (1 day). All treatments reduced the amount of viable bacteria, when measured 3 hours after the biocide dosing (FIG. 5). Killing of bacteria was most efficient in those containers where ≥15 ppm of PFA, 12 ppm of BCDMH, 45 ppm of MCDMH was added alone or where PFA was added with MCDMH.

Typical for many oxidizing biocides is that they show rapid killing of microbes, but when the oxidants have been consumed, possible survivors can show speedy re-growth in the treated water. This phenomenon was obvious also in this test. FIG. 6 shows that within 1 day active re-growth of bacteria had occurred in all those containers that had been treated with PFA, BCDMH or MCDMH only and had yielded an efficient kill (>3 log reduction of viable bacteria count). Combining of peracid and halogenated dialkylhydantoin (in this case PFA first, followed by MCDMH) showed clear synergy, the combinations were the only dosages that managed to prevent the bacterial re-growth in the circulating water for 1 day.

The invention claimed is:

1. A method for reducing microbial growth in process waters of pulp or paper production by use of a combination of chemicals consisting of a peracid and of a halogenated dialkyl hydantoin, wherein the ratio of peracid to halogenated dialkyl hydantoin is at least 2:1, the amount of the peracid compound being calculated as active agent, while the amount of halogenated dialkyl hydantoin is calculated as active chlorine, comprising:

dosing said peracid consisting of a performic acid compound into said process water, and thereafter, dosing said halogenated dialkyl hydantoin consisting of a monochlorodimethyl hydantoin into said process water, the treatment being directed to the substantially same water fraction, the interval between dosings being 10 seconds to 60 minutes, to let majority of the microbes be killed during said interval, wherein said performic acid compound is dosed in an amount of 0.2 to 45 mg/l, calculated as active agent and wherein said monochlorodimethyl hydantoin is dosed in an amount of 0.1 to 25 mg/l, calculated as active chlorine.

2. The method according to claim 1, wherein the weight ratio of the performic acid compound to monochlorodimethyl hydantoin is between 2:1 and 125:1, wherein the amount of the peracid compound being calculated as active agent, while the amount of halogenated dialkyl hydantoin is calculated as active chlorine.

3. The method according to claim 2, wherein said ratio is 2:1 to 75:1.

4. The method according to claim 1, wherein the interval between the dosages of the performic acid compound and monochlorodimethyl hydantoin is from 20 seconds to 30 minutes.

5. The method according to claim 1, wherein said process water is process water of pulp or paper production.

6. The method according to claim 1, wherein said monochlorodimethyl hydantoin is dosed in an amount of 0.2 to 15 mg/l, calculated as active chlorine.

7. The method according to claim 1, wherein said monochlorodimethyl hydantoin is dosed in an amount of 0.2 to 6 mg/l, calculated as active chlorine.

8. The method of claim 1, wherein the process water is flowing, and dosing the peracid at suction side of a pump, and the halogenated dialkyl hydantoin after the pump.

9. The method of claim 1, wherein the total amount of the peracid compound and halogenated dialkyl hydantoin is between 0.3 and 70 mg/l.

10. The method of claim 1, wherein said first dosing of performic acid increases redox of process waters.

11. A method for reducing or treating microbial re-growth in process waters of pulp or paper production by use of a combination of chemicals consisting of a performic acid compound and a monochlorodimethyl hydantoin, wherein the ratio of performic acid to monochlorodimethyl hydantoin is at least 2:1, the amount of the performic acid compound being calculated as active agent, while the amount of the monochlorodimethyl hydantoin is calculated as active chlorine, comprising: dosing said performic acid into said process water, and thereafter, dosing said monochlorodimethyl hydantoin into said process water, the treatment being directed to the substantially same water fraction, the interval between dosings being 10 seconds to 60 minutes, to let majority of the microbes be killed during said interval, wherein said performic acid compound is dosed in an amount of 0.2 to 45 mg/l, calculated as active agent and wherein said monochlorodimethyl hydantoin is dosed in an amount of 0.1 to 25 mg/l, calculated as active chlorine.

12. The method according to claim 11, wherein the method reduces or treats the bacterial regrowth in the circulating water for 1 day.

\* \* \* \* \*